United States Patent [19]

Matson et al.

[11] Patent Number: 5,171,907
[45] Date of Patent: Dec. 15, 1992

[54] PREPARATION OF HYDROGENATION CATALYST AND HYDROGENATION PROCESS THEREWITH

[75] Inventors: Michael S. Matson; Stan A. Zisman, both of Bartlesville, Okla.

[73] Assignee: Phillips Petroleum Company, Bartlesville, Okla.

[21] Appl. No.: 724,053

[22] Filed: Jul. 1, 1991

[51] Int. Cl.$^5$ ............................ C07C 5/00; C07C 5/05
[52] U.S. Cl. ...................... 585/250; 585/270; 585/271; 585/274; 585/277
[58] Field of Search ............ 585/270, 274, 277, 271, 585/250; 502/162, 161

[56] References Cited

U.S. PATENT DOCUMENTS

| | | | |
|---|---|---|---|
| 3,308,177 | 3/1967 | Atkins | 260/666 |
| 3,567,790 | 3/1971 | Morita et al. | 260/666 |
| 3,715,407 | 2/1973 | Misono et al. | 585/274 |

FOREIGN PATENT DOCUMENTS

| | | | |
|---|---|---|---|
| 702916 | 2/1965 | Canada | 585/274 |
| 1438811 | 4/1966 | France | 502/161 |
| 1603462 | 5/1971 | France | 502/161 |

OTHER PUBLICATIONS

Bull. Chem. Soc. Japan 40:2718-2719 (1967) Akira Misono and Ikuei Ogata.

Primary Examiner—Anthony McFarlane
Assistant Examiner—C. Everhart
Attorney, Agent, or Firm—Lucas K. Shay

[57] ABSTRACT

A cobalt carbonyl phosphine complex useful for hydrogenation of cyclic polyenes to corresponding cyclic monoenes is prepared by reaction of dicobalt carbonyl and a phosphine compound in at least one non-oxygenated aliphatic solvent. Selective hydrogenation of the cyclic polyenes comprises an induction period during which the polyenes are contacted with the cobalt carbonyl complex catlayst under hydrogen pressure followed by decreasing the reaction temperature and pressure for a period of time sufficient to complete the hydrogenation.

10 Claims, No Drawings

PREPARATION OF HYDROGENATION CATALYST AND HYDROGENATION PROCESS THEREWITH

FIELD OF THE INVENTION

The invention relates to a process for preparing a cobalt carbonyl phosphine complex catalyst and the use thereof for selective hydrogenation of cyclic polyenes to cyclic monoenes.

BACKGROUND OF THE INVENTION

Cyclic monoenes are useful intermediates for a number of commercial products. For example, cyclododecene is a precursor to the production of polyamides. Cyclododecene can also be converted to cyclododecanoic acid which has been used as a pesticide.

There are several techniques for converting cyclic polyenes to cyclic monoenes, but they are generally not very economically satisfactory, due to low purity of final products, low product yield, or ineffective catalyst preparation. For example, ruthenium carbonyl phosphine complex, besides its high cost, frequently requires long reaction time to reach a product purity of about 95%. In the hydrogenation of polyenes to monoenes catalyzed by cobalt carbonyl phosphine complex which is cheaper than the ruthenium complex, a higher loading of the catalyst is generally required. For example, Bulletin of Chemical Society of Japan, Vol. 40, No. 11, pp. 2718-2719 (1967) discloses that, in order to get a high selectivity to cyclodecene, it requires a high catalyst loading of 9.94 g of cobalt tricarbonyl tributylphosphine per mole of cyclododecatriene.

Additionally, the aforementioned reference discloses preparing the cobalt complex catalyst using benzene or diethyl ether. The cobalt carbonyl phosphine complex is partially soluble in these solvents and so it cannot be effectively separated from the solution mixture, resulting in reducing the recovery of the catalyst and in contaminating the catalyst which, in turn, has lowered catalytic activity. Furthermore, the use of benzene should be discouraged because of its potential carcinogenicity.

SUMMARY OF THE INVENTION

It is therefore an object of the invention to prepare a cobalt carbonyl phosphine catalyst having high selectivity in the hydrogenation of cyclic polyenes.

Another object of the invention is to prepare the cobalt carbonyl phosphine catalyst in high yield.

Yet another object of the invention is to provide a process for catalytically converting the cyclic polyenes to corresponding monoenes in high selectivity using the cobalt carbonyl phosphine complex catalyst.

Still a further object of the invention is to provide a hydrogenation process employing the improved catalyst in high yield.

Other objects of this invention will be apparent from the written description and the appended claims.

According to the present invention, a process for preparing a cobalt carbonyl phosphine complex useful for selective hydrogenation of cyclic polyenes to cyclic monoenes comprises: (1) dissolving dicobalt octacarbonyl in at least one non-oxygenated aliphatic solvent to form a solution; (2) adding a phosphine compound in at least one non-oxygenated aliphatic solvent to the solution and mixing to form a mixture containing the cobalt carbonyl phosphine complex; (3) separating the complex from the mixture; and (4) recovering the cobalt carbonyl phosphine complex.

According to another embodiment of the invention, a process for selective hydrogenation of cyclic polyenes to cyclic monoenes comprises: (1) contacting a cyclic polyene under hydrogen pressure, during an induction period, with a hydrogenation catalyst comprising cobalt carbonyl phosphine complex, which is prepared by the reaction product of a phosphine and dicobalt octacarbonyl in at least one non-oxygenated aliphatic solvent followed by separation, under conditions sufficient to selectively hydrogenate the polyene; (2) decreasing the hydrogen pressure after the induction period; and (3) separating the resulting monoene from the catalyst.

DETAILED DESCRIPTION OF THE INVENTION

According to the invention, a hydrogenation catalyst having high activity comprising a cobalt carbonyl phosphine complex useful for selective hydrogenation of cyclic polyenes to cyclic monoenes is prepared in high yield by dissolving dicobalt octacarbonyl in a non-oxygenated aliphatic solvent followed by adding and mixing a phosphine solution. The catalyst is then separated from the resulting mixture.

The cobalt carbonyl phosphine complexes prepared by the inventive process have a general formula of $(Co(CO)_3PR(R')(R''))_2$ wherein R, R' and R'' are same or different alkyl, cycloalkyl, or aryl groups having 1 to 9 carbon atoms.

Examples of suitable cobalt carbonyl phosphine complexes include cobalt tricarbonyl tri-n-butylphosphine, cobalt tricarbonyl cyclohexylphosphine, cobalt tricarbonyl tritolylphosphine, cobalt tricarbonyl triphenylphosphine, cobalt tricarbonyl trimethylphosphine, cobalt tricarbonyl triethylphosphine, cobalt tricarbonyl triisopropylphosphine, and cobalt tricarbonyl tri-n-propylphosphine, and mixtures thereof.

The non-oxygenated aliphatic solvent has low boiling point, can be a linear or branched hydrocarbon, and has about 4 to 10 carbon atoms. The cobalt carbonyl phosphine complex should be essentially insoluble in the non-oxygenated aliphatic solvent. However, the dicobalt carbonyl should be substantially soluble in the solvent.

Examples of the non-oxygenated aliphatic solvent include pentane, hexane, heptane, octane, nonane, decane, cyclohexane, methylcyclopentane, and methylcyclohexane, and mixtures thereof.

The phosphine compound employed to prepare the catalyst has a general formula of $PR(R')(R'')$ wherein R, R' and R'' are same or different alkyl, cycloalkyl, or aryl groups having about 1 to 9 carbon atoms.

Exemplary of the phosphine compounds are tricyclohexylphosphine, tri-n-butylphosphine, tri-isobutylphosphine, dicyclohexylphenylphosphine, diethylphenylphosphine, tricyclohexylphosphine, tribenzylphosphine, ortho-tolyldiphenylphosphine, and di(ortho-tolyl)phenylphosphine, and mixtures thereof. Preferred is tri-n-butyl phosphine.

The cyclic polyenes that can be employed in the practice of this invention comprise any polyunsaturated olefin having at least 6 carbon atoms and at least 2 ethylenic double bonds. Suitable cyclic polyenes include 1,5,9-cyclododecatriene, 1,5-cyclodecadiene, 4-n-butylcyclododecatriene, 2.4-dimethylcyclododecatriene, 1-cyclohexylcyclododecatriene, 1-phenylcyclododecatriene, 1,5-cyclooctadiene, 1,4-cyclooctadiene, 1,4-cyclohexadiene, 1,3-cyclohexadiene, bicyclo[2.2.1]hepta-2.5-diene, bicyclo[2.2.2]octa-2,5-diene, and the like, and mixtures thereof.

The cobalt carbonyl phosphine complex of the invention can be prepared, for instance, in the following fashion. To a proper container, such as a flask, that is equipped with an agitation means, such as a power stirrer, an addition means, such as an addition funnel, and a reflux condenser with an inert gas inlet, is charged with dicobalt octacarbonyl and a non-oxygenated aliphatic solvent, such as pentane. The mole ratio of the solvent to the dicobalt octacarbonyl is about 20 to 100, preferably 30 to 60 for easier recovery and reuse of the solvent. Although it can be done at elevated temperature and pressure, it is preferred to dissolve the dicobalt octacarbonyl in the solvent under ambient temperature and atmospheric pressure.

A solution of a phosphine compound in the non-oxygenate aliphatic solvent is then added slowly to the dicobalt carbonyl solution which is being constantly mixed by an agitation means, such as stirring. This aliphatic solvent can be the same as or different from that used to dissolve the dicobalt octacarbonyl. The mole ratio of the phosphine compound to the dicobalt octacarbonyl is about 1.5 to 3.0, preferably about 2.0. The mole ratio of the solvent, used in the phosphine solution, to the dicobalt octacarbonyl is about 5 to 30, preferably 10 to 20.

Upon completion of the addition of the phosphine solution, a precipitate is formed. The mixture is agitated for an additional length of time ranging from 5 minutes to 5 hours, preferably 10 minutes to 3 hours, and most preferably 15 minutes to 2 hours, to ensure complete reaction for better catalytic activity.

The precipitate is then separated from the solvent by a separation means, such as filtration, centrifugation or decantation. The solid fraction is washed at least once with a non-oxygenated aliphatic solvent. Generally the same type of solvent used in the reaction is used in the wash. If pentane is used in the reaction, then it is used in the wash. The mole ratio of the solvent, used in the washing, to the dicobalt octacarbonyl is about 50 to about 120, preferably 70 to 90. The washed catalyst is then dried by a drying means, such as vacuum drying.

In another embodiment of the invention, the dicobalt carbonyl phosphine complex is used to selectively hydrogenate a cyclic polyene to its corresponding cyclic monoene. The polyene and cobalt catalyst are charged to a reaction zone such as a stainless steel autoclave equipped with external electric heater, internal heating and cooling coils, gas inlet, and power stirrer. The mole ratio of the catalyst to the polyene is about 0.0001 to 0.020, preferably 0.0005 to 0.010, and most preferably 0.001 to 0.006 to obtain the best conversion of the polyene, as well as, the best yield and selectivity of the monoene desired.

The reactor is generally purged with an inert gas such as nitrogen and then hydrogen. Proper agitation is initiated with heating. At the internal temperature of about 80° to about 120° C., the reactor pressure is elevated to about 100 to about 500 psig, preferably about 200 to about 400 psig. hydrogen. The reactor temperature is then increased to and held at about 100° to about 200° C., preferably about 135° to about 160° C., for about 20 minutes to about 10 hours, preferably about 40 minutes to about 7 hours.

After this induction period, the reactor pressure is then set at about 120 to about 280 psig, preferably 130 to about 180 psig hydrogen and the reactor temperature is set at about 130° to about 150° C. until the hydrogenation is complete.

Upon cooling to about 20° to 60° C., the reactor contents are removed from the reactor and the product is separated by a suitable separation means, such as distillation.

The following non-limiting examples are provided to further illustrate the practice of the present invention.

EXAMPLE I

This example illustrates that the inventive process for preparing the cobalt carbonyl phosphine complex has very high yield.

The cobalt complex catalyst was synthesized in the following fashion. A 200-mL, three-necked, round-bottomed flask equipped with a power stirrer, an addition funnel, and a reflux condenser with $N_2$ inlet was charged with dicobalt octacarbonyl (8.55 g, 0.025 moles) and pentane (75 ml) to form a solution. At room temperature, a solution of tri-n-butylphosphine (94%, 10.76 g, 0.05 moles) in pentane (25 ml) was added to the stirred purple solution which resulted in a slight exotherm with evolution of carbon monoxide and the formation of a yellow precipitate. After completion of the addition, the mixture was stirred for an additional hour and then filtered. Following a pentane wash (150 ml), the solid was dried under vacuum to afford 17.1 g (98.8%) of a yellow powder.

COMPARATIVE EXAMPLE I

This comparative example illustrates that a solvent that solubilizes the catalyst fails to give a satisfactory catalyst isolation.

The experiment was carried out the same as that described in Example I except that diethyl ether was used as solvent. Because the catalyst is partially solubilized in the ether, it could not be quantitatively isolated and purified by the process described in Example I and had to be recovered by concentration, i.e., by stripping off the ether resulting in contamination with reactants.

COMPARATIVE EXAMPLE IA

This comparative example follows a process that has been disclosed in prior art (Bull. Chem. Soc. Japan 40:2718-2719, 1967) for preparing the cobalt carbonyl phosphine complex using diethyl ether as solvent. It suggests that the referenced process has a very low yield, because the catalyst is partially soluble in ether and cannot be isolated by filtration.

To a flask, equipped the same as that described in Example I, that contained a solution of dicobalt octacarbonyl (17.1 g, 0.05 moles) in diethyl ether (20 ml), was added tri-n-butylphosphine (94%, 20.23 g, 0.1 moles) in ether (5 ml) under nitrogen at room temperature for 20 minutes. Following the addition of 15 ml more ether, the slurry was stirred an additional 30 minutes. The ether was then stripped of by vacuum drying to afford 39 g of brownish product mix, that was determined to be $Co_2P_2O_6C_{30}H_{54}$ and was greater than the theoretical yield of 34.52 g because impurities such as the phosphine compound were carried through.

The results of this comparative example and of Example I indicate that the inventive process produces a pure form of catalyst which is free from feedstock contamination.

EXAMPLE II

This example illustrates the hydrogenation of a cyclic polyene to its corresponding cyclic monoene with high purity using the inventive process and catalyst.

A typical hydrogenation of the 1,5,9-cyclododecatriene was performed as follows. A 300 cc autoclave was charged with the triene (162.3 g, 1 mole) and the cobalt complex catalyst (2.0 g). After the system had been first purged with $N_2$ twice then $H_2$ once, an induction period was initiated with stirring (1000 rpm) and heating. At an internal temperature of about 100° C., the reactor pressure was elevated to 300 psig $H_2$ and the temperature increased to the desired level (140°-145° C.) for about 0.75-7.0 h. At the end of this induction period, the pressure and the temperature were then set to 150 psig $H_2$ and 140° C., respectively, until the hydrogenation was complete. After the solution was allowed to cool, the contents were removed and then distilled to separate the catalyst. No variance was observed in the gas chromatographic analyses between the crude and the distilled product. The results are shown in Table I.

TABLE I[a]

| Run No. | Catalyst Loading (g/mol CDT) | Induction Period | | | Reaction | | | Purity | | |
|---|---|---|---|---|---|---|---|---|---|---|
| | | Temp. (°C.) | Pressure (psig) | Time (h) | Temp. (°C.) | Pressure (psig) | Time (h) | Mono-ene | Di-, Tri-enes | Saturate |
| 1 | 2 | 140 | 300 | 0.8 | 140 | 150 | 13.8 | 97.17 | 0.64 | 2.19 |
| 2 | 2 | 140 | 300 | 0.8 | 140 | 150 | 12.9 | 96.66 | 0.82 | 2.52 |
| 3 | 2 | 145 | 300 | 1.0 | 140 | 150 | 13.1 | 96.01 | 1.82 | 2.17 |
| 4 | 2 | 140 | 300 | 7.1 | 140 | 150 | 3.3 | 95.64 | 0.92 | 3.44 |
| 5 | 2 | 140 | 300 | 2.0 | 140 | 150 | 13.3 | 96.33 | 0.67 | 3.00 |
| 6 | 2 | 140 | 300 | 3.0 | 140 | 150 | 11.7 | 96.29 | 0.69 | 3.02 |

[a]Gas Chromatographic Analyses were performed at 90° C. (constant) using a GC equipped with a TCEP column and a flame ionization detector.

The results shown in Table I indicate that several factors influence the performance of the catalyst: loading, temperature, pressure, and the induction period of the catalyst itself. A loading of 2.0 g catalyst/mole triene was found to be the minimum at which material of 95% specified purity could be obtained. A maximum temperature of 145° C. was employed because higher temperatures result in the formation of excessive cyclic impurities and overhydrogenation. The pressure was varied during each run to provide a maximum rate of reaction while minimizing overhydrogenation which reduces selectivity. It was demonstrated that this cobalt complex requires an induction period at an elevated pressure of about 300 psig $H_2$ in order to initiate a moderate rate of reaction. Following this induction period, the pressure could then be lowered (150 psig $H_2$) until completion of the hydrogenation.

COMPARATIVE EXAMPLE II

These comparative runs were carried out the same as those described in Bull. Chem. Soc. Japan 40: 2718-2719, 1967 with the exception that toluene was used as solvent and the catalyst prepared in Comparative Example IA was used.

TABLE II[a]

| Run No. | Catalyst Loading (g/mol CDT) | Induction Period | | | Reaction | | | Purity | | |
|---|---|---|---|---|---|---|---|---|---|---|
| | | Temp. (°C.) | Pressure (psig) | Time (h) | Temp. (°C.) | Pressure (psig) | Time (h) | Mono-ene | Di-, Tri-enes | Saturate |
| 7[b,c] | 10 | —[d] | — | — | 150 | 500 | 3.0 | 98.1 | 0 | 1.7 |
| 8[e] | 2 | — | — | — | 150 | 500 | 2.7 | 89.5 | 0 | 10.4 |

[a]Gas Chromatographic Analyses were performed at 90° C. using a GC equipped with a TCEP column and a flame ionization detector.
[b]The run conditions were the same as those described in Bull. Chem. Soc. Japan 40 (11): 2718-2719 (1967).
[c]Run was made in toluene as solvent.
[d]—, No induction period.
[e]Run was carried out without using a solvent.

Table II shows that in order to achieve a high product purity, the catalyst loading of the catalyst prepared by referenced process must be high (10 g/mol CDT, run 7) and the process must be carried out at high pressure. Table II also shows that, if the catalyst loading is low (2 g/mol CDT, run 8), a very unsatisfactory result was obtained (89.5% product purity) even at 500 psig high pressure.

COMPARATIVE EXAMPLE IIA

This comparative example illustrates that, even using the inventive hydrogenation process, the catalyst prepared by the prior art method (Bull. Chem. Soc. Japan 40: 2718-2719, 1967) produces a product having low purity.

The runs were carried out the same as those described in Example II with the exception that the catalyst used was prepared according to comparative Example IA and that the pressure during hydrogenation was 250 psig. The results are shown in Table III.

TABLE III[a]

| Run No. | Catalyst Loading (g/mol CDT) | Induction Period | | | Reaction | | | Purity | | |
|---|---|---|---|---|---|---|---|---|---|---|
| | | Temp. (°C.) | Pressure (psig) | Time (h) | Temp. (°C.) | Pressure (psig) | Time (h) | Mono-ene | Di-, Tri-enes | Saturate |
| 9 | 2 | 140 | 300 | 2.3 | 140 | 250 | 5.3 | 94.0 | 0.5 | 4.7 |

TABLE III-continued

| Run No. | Catalyst Loading (g/mol CDT) | Induction Period | | | Reaction | | | Purity | | |
|---|---|---|---|---|---|---|---|---|---|---|
| | | Temp. (°C.) | Pressure (psig) | Time (h) | Temp. (°C.) | Pressure (psig) | Time (h) | Mono-ene | Di-, Tri-enes | Saturate |
| 10 | 2 | 140 | 300 | 2.3 | 140 | 200 | 9.8 | 94.0 | 0.6 | 4.8 |

<sup>a</sup>Gas Chromatographic Analyses were performed at 90° C. on using a GC equipped with a TCEP column and a flame ionization detector.

Table III shows that even with 2.3 hour induction period and 250 psig pressure, the product had a low purity of 94% (run 9). Increasing the reaction time failed to increase the product purity (run 10). These results demonstrate that a successful hydrogenation, i.e., producing a product having greater than the critical 95% purity, require an active catalyst and hydrogenation process prepared by the inventive processes.

Collectively, the results shown in above examples indicate that the invention provides an easy process for preparing a pure form of catalyst in near quantitative yield; a lower catalyst loading, if in pure form, is required to achieve comparable product purity; and that the catalyst prepared by the prior art process results in substantial difficulty in catalyst recovery and purification.

The examples have been provided merely to illustrate the practice of the invention and should not be read so as to limit the scope of the invention or the appended claims in any way. Reasonable variations and modifications, not departing from the essence and spirit of the invention, are contemplated to be within the scope of patent protection desired and sought.

That which is claimed is:

1. A process for selective hydrogenation of a cyclic polyene to a cyclic monoene comprising:
    (a) contacting said cyclic polyene under hydrogen pressure, during an induction period, with a hydrogenation catalyst comprising a cobalt carbonyl phosphine complex, prepared by reacting a phosphine and dicobalt octacarbonyl in at least one non-oxygenated aliphatic solvent, under conditions sufficient to selectively hydrogenate said polyene;
    (b) decreasing said hydrogen pressure after said induction period and continuing said hydrogenation; and thereafter
    (c) separating said monoene from said catalyst.

2. A process according to claim 1 wherein:
    said cyclic polyene is a polyunsaturated olefin having at least 6 carbon atoms and at least 2 ethylenic double bonds;
    said cobalt carbonyl phosphine complex has a general formula of (Co(CO)$_3$PR(R')(R''))$_2$ wherein R, R' and R'' are same or different alkyl, cycloalkyl or aryl groups having 1 to 9 carbon atoms;
    said aliphatic solvent of (a) and of (b) is a linear or branched hydrocarbon having about 4 to 10 carbon atoms;
    said phosphine compound has general formula of PR(R')(R'') wherein R, R' and R'' are same or different alkyl, cycloalkyl and aryl groups having about 1 to 9 carbon atoms.

3. A process according to claim 2 wherein said cyclic polyene is selected from the group consisting of 1,5,9-cyclododecatriene, 1,5-cyclodecadiene, 4-n-butylcyclododecatriene, 2,4-dimethylcyclododecatriene, 1-cyclohexylcyclododecatriene, 1-phenylcyclododecatriene, 1,5-cyclooctadiene, 1,4-cyclooctadiene, 1,4-cyclohexadiene, 1,3-cyclohexadiene, bicyclo[2.2.1]hepta-2,5-diene, bicyclo[2.2.2]octa-2,5-diene, and the like and mixtures thereof;
    said cobalt carbonyl phosphine complex is selected from the group consisting of cobalt tricarbonyl tri-n-butylphosphine, cobalt tricarbonyl cyclohexylphosphine, cobalt tricarbonyl tritolylphosphine, cobalt tricarbonyl triphenylphosphine, cobalt tricarbonyl trimethylphosphine, cobalt tricarbonyl triethylphosphine, cobalt tricarbonyl triisopropylphosphine, and cobalt tricarbonyl tri-n-propylphosphine, and mixtures thereof;
    said aliphatic solvent of (a) and of (b) is selected from the group consisting of pentane, hexane, heptane, octane, nonane, decane, cyclohexane, methylcyclopentane, and methylcyclohexane, and mixtures thereof;
    said phosphine compound is selected from the group consisting of tricyclohexylphosphine, tri-n-butylphosphine, tri-isobutylphosphine, dicyclohexylphenylphosphine, diethylphenylphosphine, dicyclohexylphosphine, tribenzylphosphine, orthotolyldiphenylphosphine, and di(ortho-tolyl)phenylphosphine, and mixtures thereof.

4. A process according to claim 3 wherein said cyclic polyene is 1,5,9-cyclododecatriene; said cobalt carbonyl phosphine complex is cobalt tricarbonyl tri-n-butylphosphine; said aliphatic solvent of (a) and of (b) is pentane; and said phosphine is tri-n-butylphosphine.

5. A process according to claim 3 wherein said hydrogen pressure of (a) is about 100 to about 500 psig; and said hydrogen pressure of (b) is about 120 to about 280 psig.

6. A process according to claim 5 wherein said hydrogen pressure of (a) is about 200 to about 400 psig at a temperature in the range of about 135° to about 160° C.; and wherein said hydrogen pressure of (b) is about 130 to about 180 psig at a temperature set at about 130° to about 150° C.

7. A process according to claim 1 wherein step (a) is carried out at 300 psig hydrogen pressure at 140°-145° C. for about 0.75-7.0 hours; and wherein step (b) is carried out at 150 psig hydrogen pressure at 140° C. for 3.3 to 13.8 hours.

8. A process according to claim 1 wherein said catalyst is present in the amount, in terms of mole ratio of said catalyst to said polyene, of about 0.0001 to 0.020.

9. A process according to claim 8 wherein said mole ratio is 0.0005 to 0.010.

10. A process for selective hydrogenation of 1,5,9-cyclododecatriene to cyclododecene comprising: (a) contacting said 1,5,9-cyclododecatriene with 2 grams of cobalt tricarbonyl tri-n-butylphosphine per mole of said 1,5,9-cyclododecatriene under a hydrogen pressure of 300 psig at 140° C. to 145° C. for about 0.75-7.0 hours; (b) thereafter decreasing said hydrogen pressure to and holding at 150 psig at 150° C. for 3.3 hours to 13.8 hours; and (c) separating said cyclododecene from said cobalt tricarbonyl tri-n-butylphosphine.

* * * * *